US00PP37279P2

(12) United States Plant Patent
Warner

(10) Patent No.: US PP37,279 P2
(45) Date of Patent: Feb. 24, 2026

(54) SHRUB ROSE PLANT NAMED 'CHEWGOLDRUSH'

(50) Latin Name: ***Rosa* hybrid**
Varietal Denomination: CHEWGOLDRUSH

(71) Applicant: Spring Meadow Nursery, Grand Havem, MI (US)

(72) Inventor: Christopher Hugh Warner, Newport (GB)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 18/977,478

(22) Filed: Dec. 11, 2024

(51) Int. Cl.
*A01H 5/02* (2018.01)

(52) U.S. Cl.
USPC ..... Plt./104

(58) Field of Classification Search
USPC ..... Plt./104, 111, 118, 134, 145
CPC . A01H 5/02; A01H 5/00; A01H 6/749; A01H 6/74
See application file for complete search history.

(56) References Cited

U.S. PATENT DOCUMENTS

PP18,473 P2 * 2/2008 Carruth ..... A01H 5/02 Plt./145

* cited by examiner

*Primary Examiner* — June Hwu

(57) ABSTRACT

A new and distinct cultivar of *Rosa* plant named 'Chew-GoldRush' is disclosed, characterized by sprays of bright yellow flowers and dark green, glossy foliage. Flower occurs freely. Plants are shrublike, compact, exceptionally healthy, with a very high resistance to a number of common rose diseases. The new cultivar is a *Rosa*, suitable for ornamental garden purposes.

2 Drawing Sheets

Latin name of the genus and species: *Rosa* hybrid.
Variety denomination: 'CHEWGOLDRUSH'.

BACKGROUND OF THE INVENTION

The new cultivar is a product of a planned breeding program by the inventor to develop new *Rosa* varieties with good health and tolerance to rose diseases, strong flower color, floriferousness and fragrance. The seed parent is the unpatented variety *Rosa* 'Tan01366'. The pollen parent is the unpatented variety *Rosa* 'Gardeners Glory'. The crossing resulting in the new cultivar was made in May 2010 at a nursery in Newport, United Kingdom.

*Rosa* 'CHEWGOLDRUSH' was found and selected in the spring of 2011 in Newport, United Kingdom. The first asexual propagation of occurred in July 2012 by softwood cuttings at the same nursery, and 'CHEWGOLDRUSH' has been found to retain its distinctive characteristics through successive asexual propagations over multiple generations.

SUMMARY OF THE INVENTION

The cultivar 'CHEWGOLDRUSH' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CHEW-GOLDRUSH'. These characteristics in combination distinguish 'CHEWGOLDRUSH' as a new and distinct *Rosa* cultivar:

1. Bright, stable yellow flower color.
2. Free flowering.
3. Fairly quick reblooming.
4. Exceptionally healthy; very high resistance to a number of common rose diseases.
5. Dark green, glossy foliage.
6. Compact, shrub-like habit.

COMPARISON TO PARENT VARIETIES

'CHEWGOLDRUSH' is similar in most horticultural characteristics to the seed parent. Plants of the new cultivar 'CHEWGOLDRUSH' however differ in the following:

1. Flower color of the new variety is medium yellow, while the flower color of the seed parent is orange fading to cream.
2. Fragrance of the new variety is citrusy and perfume-like, while the fragrance of the seed parent is aromatic.

'CHEWGOLDRUSH' is similar in most horticultural characteristics to the pollen parent. Plants of the new cultivar 'CHEWGOLDRUSH' however differ in the following:

1. Flower color of the new variety is medium yellow, while the flower color of the pollen parent is light yellow.
2. Fragrance of the new variety is stronger than the fragrance of the pollen parent.
3. Foliage of the new variety is glossy, while the foliage of the pollen parent is semi-glossy.
4. Plants of the new variety are more disease-resistant than plants of the pollen parent.
5. Plants of the new variety have fewer thorns than plants of the pollen parent.

COMMERCIAL COMPARISON

'CHEWGOLDRUSH' can be compared to the commercial variety *Rosa* 'WEKvossutono', U.S. Plant Pat. No.

18,473. Plants of the new cultivar 'CHEWGOLDRUSH' are similar to plants of 'WEKvossutono' in most horticultural characteristics. Plants of the new cultivar 'CHEWGOLDRUSH', however, differ in the following:

1. Fragrance of the new variety is more intense than the fragrance of this comparator.
2. Fragrance of the new variety is citrusy and perfume-like, while the fragrance of this comparator is of mild licorice.
3. Flower color of the new variety ages to pale yellow, while the flower color of this comparator ages to pale yellow-orange.

BRIEF DESCRIPTION OF THE PHOTOGRAPHS

'CHEWGOLDRUSH' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rosa*.

DETAILED BOTANICAL DESCRIPTION

Figure 1:
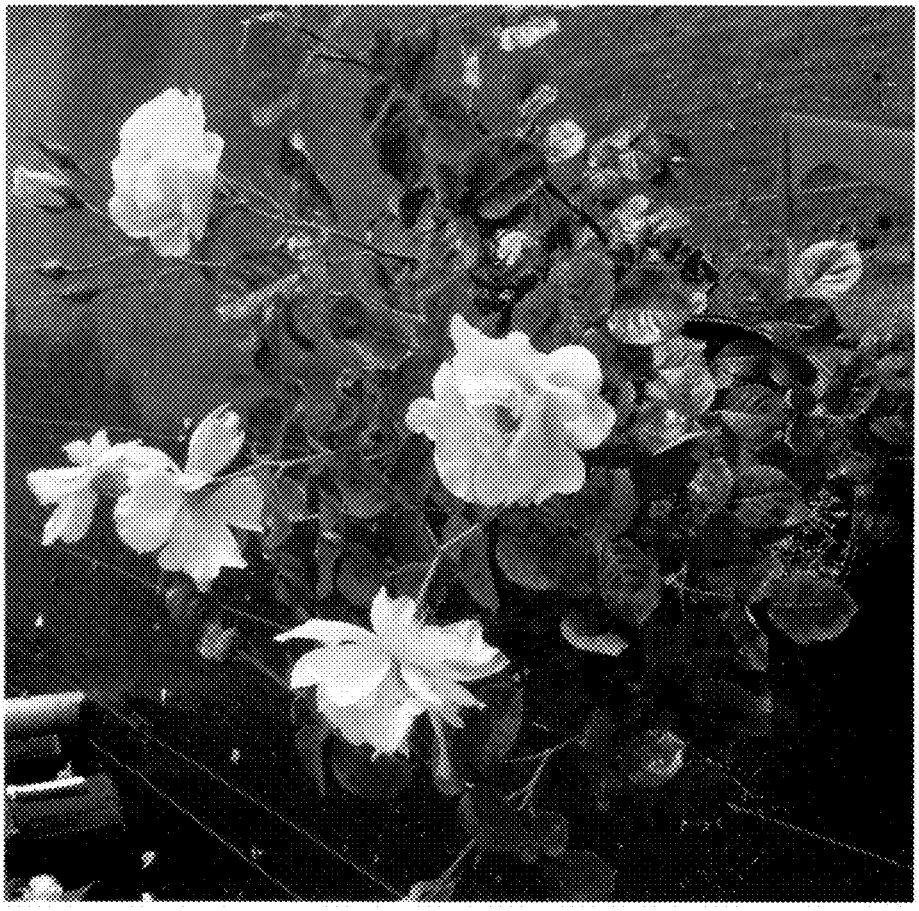
FIG. 1 is a photograph of a 1.5 year old plant of 'CHEWGOLDRUSH' in a 3-gallon container grown in Grand Haven, MI.
Figure 2:
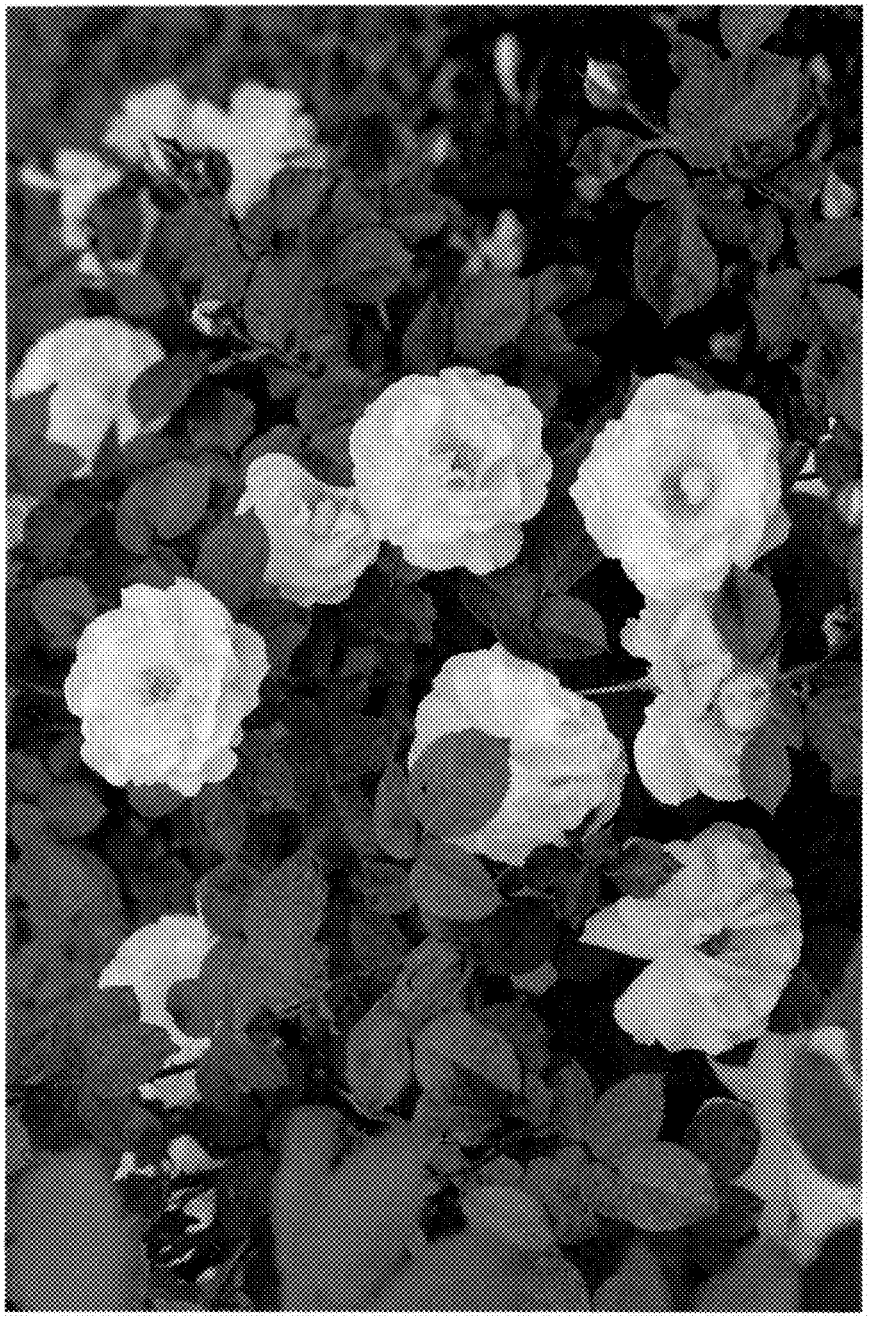
FIG. 2 is a close-up view of multiple flowers of 'CHEWGOLDRUSH'.

The following is a detailed description of the botanical characteristics of the new and distinct *Rosa* 'CHEWGOLDRUSH'. The detailed description was taken on a 3-year-old container-grown plant in Grand Haven, Michigan in 2024. All colors cited herein refer to The Royal Horticultural Society Colour Chart (The Royal Horticultural Society (R.H.S.), London, 2015 Edition). Where specific dimensions, sizes, colors, and other characteristics are given, it is to be understood that such characteristics are approximations or averages set forth as accurately as is practicable.

Botanical classification: *Rosa* hybrid 'CHEWGOLDRUSH'.

*Commercial classification.*—Shrub rose.

PROPAGATION

Typical method: Softwood cuttings.

Root description: Dense, fibrous and fleshy, moderately branching, medium thickness. White in color, not accurately measured with an R.H.S. chart.

Time to initiate rooting: 30 days in summer at 20° C.

Time to produce a rooted young plant: 120 days in summer at 20° C.

PLANT

Plant type: Perennial.

Plant shape: Upright, compact.

Growth habit: Upwards and outwards.

Height: 60 cm.

Width: 55 cm.

Growth rate: Moderate to high.

Vigor: Very vigorous.

Branching habit:

Stem:

*Branching.*—Basal, some pinching required.

*Number of lateral branches.*—10 to 15.

*Shape.*—Rounded and glabrous, with some thorns.

*Color.*—RHS Yellow-Green 144A with a Greyed-Orange 176B tint.

*Length.*—40 cm.

*Width.*—5 mm.

*Aspect.*—40° to 80°.

*Strength.*—Very strong, especially old wood.

*Pubescence.*—Very slight, on new growth only.

Internode length: 3.75 cm.

Thorns:

*Number.*—0 to 1 per linear cm.

*Shape.*—Unguiculate (claw-like), slightly curved towards the base of the lateral branch.

*Apex.*—Acicular.

*Length, base.*—7 mm.

*Height.*—7 mm.

*Color.*—Immature: RHS Greyed-Purple 187B. Mature: RHS Greyed-Purple 187B.

FOLIAGE

Leaf:

*Arrangement.*—Alternate.

*Quantity.*—6 to 8 per lateral branch.

*Length.*—14 cm.

*Width.*—9 cm.

Leaflet:

*Quantity.*—3 to 5 per leaf.

*Shape.*—Broadly elliptic to orbicular.

*Apex.*—Broadly acuminate.

*Base.*—Obtuse.

*Terminal length.*—5.5 cm.

*Terminal width.*—4.5 cm.

*Lateral length.*—Upper pair: 5 cm. Lower pair: 4 cm.

*Lateral width.*—Upper pair: 4 cm. Lower pair: 3 cm.

*Margin.*—Serrate to doubly serrate. Very weak marginal undulation.

*Color.*—Young, upper surface: RHS Yellow-Green 146A. Young, under surface: RHS Yellow-Green 146B. Mature, upper surface: RHS Green NN137A. Mature, under surface: RHS Yellow-Green 147B.

*Texture.*—Glabrous, slightly coriaceous upper and lower surfaces.

*Pubescence.*—None upper and lower surfaces.

*Venation.*—Pattern: Pinnate. Color, upper side: RHS Yellow-Green 144C. Color, under side: RHS Yellow-Green 144C.

Petiole:

*Length.*—Leaf: 4 cm. Leaflet: 2 mm.

*Diameter.*—Leaf: 2 mm. Leaflet: 1 mm.

*Color, leaf.*—Upper side: RHS Yellow-Green 144A with a slight Greyed-Orange 176B tint. Under side: RHS Yellow-Green 144A.

*Color, leaflet.*—Upper side: RHS Yellow-Green 144A with a slight Greyed-Orange 176B tint. Under side: RHS Yellow-Green 144A.

*Texture.*—Leaf: Both sides glabrous, with some small thorns. Leaflet: Both sides glabrous.

Stipule:

*Quantity.*—2.

*Shape.*—Acicular.

*Apex*.—Acute.
*Base*.—Fused.
*Margin*.—Entire to slightly cilliate.
*Length*.—2.5 cm.
*Width*.—2 mm.
*Texture*.—Both surfaces glabrous.
*Color*.—Upper surface: RHS Yellow-Green 147B. Lower surface: RHS Yellow-Green 147B.

FLOWER

Natural flowering season: Summer (May to July).
Arrangement: Terminal sprays (determinate racemes) of 5 to 7 buds and flowers.
Flower form: Double flower, whorled.
Spray height: 12 cm.
Spray width: 20 cm.
Flowers per spray: 5 to 7.
Sprays per lateral stem: 1 to 2.
Fragrance: Bright citrus scent with floral, perfume-like elements which evoke an old rose fragrance; moderate intensity.
Bud:
*Length*.—3 cm.
*Width*.—1.2 cm.
*Shape*.—Ovate.
*Color*.—RHS Yellow-Green 146A to 146B.
Flowers:
*Shape*.—Round whorl.
*Aspect*.—Upright and outward.
*Diameter*.—10 cm.
*Depth*.—4 cm.
*Longevity*.—2 weeks on plant.
*Persistence*.—Self-cleaning.
*Profile of lower part*.—Flattened convex.
Petals:
*Appearance*.—Delicate, silky, soft.
*Arrangement*.—Double whorl.
*Number*.—15 to 20.
*Length*.—4.5 cm.
*Width*.—5 cm.
*Shape*.—Obovate.
*Apex*.—Obtuse to emarginate.
*Base*.—Obtuse.
*Margin*.—Entire.
*Color*.—When opening, upper side: RHS Yellow-Orange 15A. When opening, under side: RHS Yellow-Orange 15A. Fully opened, upper side: RHS Yellow 11A. Fully opened, under side: RHS Yellow 11A. Fading, upper side: RHS Yellow 10A. Fading, under side: RHS Yellow 10A. Basal spot: None upper or lower.
*Texture*.—Upper: Silky and smooth. Lower: Silky and smooth.
Petaloids:
*Appearance*.—Petaloids are generally well-formed and closely resemble primary petals; however, the very innermost petaloids are somewhat irregularly shaped with a folded appearance.
*Arrangement*.—Whorl.
*Number*.—5 to 10.
*Length*.—3.5 cm.
*Width*.—1.5 cm.
*Shape*.—Irregularly shaped with a tendency to fold upon itself, though most are narrowly obovate.
*Margin*.—Irregularly lobed/notched.
*Color*.—Immature: RHS Yellow-Orange 15A. Mature: RHS Yellow 11A.
Sepals:
*Appearance*.—Curved toward stem.
*Number*.—5.
*Arrangement*.—Whorl (stellate).
*Length*.—3 cm.
*Width*.—1 cm.
*Shape*.—Triangular.
*Apex*.—Sharply acuminate.
*Base*.—Fused.
*Amount of sepal extension*.—Absent.
*Margin*.—Entire.
*Color*.—Immature, upper side: RHS Green 138B. Immature, under side: RHS Yellow-Green 146A to 146B. Mature, upper side: RHS Green 138B. Mature, under side: RHS Yellow-Green 146A to 146B.
*Texture*.—Upper side: Soft and pubescent. Under side: Coarse and slightly prickly.
Calyx:
*Length*.—3 cm.
*Diameter*.—2 cm.
*Shape*.—Collar-like with downward-curved sepals.
Peduncle:
*Length*.—5 cm.
*Diameter*.—4 mm.
*Angle*.—45° to 60°.
*Strength*.—Strong, somewhat flexible.
*Color*.—RHS Yellow Green 144A.
*Texture*.—Somewhat prickly with the occasional small, short thorn.
Pedicel:
*Length*.—5 cm.
*Diameter*.—2.5 mm.
*Angle*.—45° to 60°.
*Strength*.—Strong, somewhat flexible.
*Color*.—RHS Yellow Green 144C flushed Greyed-Orange 173B.
*Texture*.—Somewhat prickly with the occasional small, short thorn.

REPRODUCTIVE ORGANS

Gynoecium:
*Pistil number*.—About 30.
*Pistil length*.—1 cm.
*Stigma shape*.—Peltate.
*Stigma color*.—RHS Yellow 7C.
*Style length*.—1 cm.
*Style color*.—RHS Yellow-Green 144D at the base, becoming tinted with Greyed-Orange 176B towards the top.
*Receptacle height*.—1 cm.
*Receptacle diameter*.—0.75 cm.
*Receptacle shape*.—Ovoid/Spherical.
*Receptacle texture*.—Glabrous.
*Receptacle color*.—RHS Yellow-Green 144A.
Androecium:
*Stamen number*.—About 100.
*Anther shape*.—Reniform.
*Anther length*.—3 mm.
*Anther color*.—RHS Yellow-Orange 16A.
*Filament color*.—RHS Yellow-Orange 16A.

*Amount of pollen*.—Moderate.

*Pollen color*.—RHS Yellow 8D.

OTHER CHARACTERISTICS

Fruit and seed: Not observed to date.

Disease and pest resistance: Displays an above average resistance to powdery mildew, downy mildew, black spot and rust as compared to other commercial cultivars, especially other yellow roses.

Temperature tolerance: Tolerant to USDA Zones 4-9. Excellent tolerance to rain. Foliage exhibits excellent durability to stress.

What is claimed is:

1. A new and distinct cultivar of *Rosa* plant named 'ChewGoldRush' as herein illustrated and described.

* * * * *